US011786466B2

(12) United States Patent
Hasson et al.

(10) Patent No.: US 11,786,466 B2
(45) Date of Patent: Oct. 17, 2023

(54) TOPICAL FORMULATIONS FOR TREATING DERMATOLOGICAL DISORDERS INCLUDING MALE PATTERN BALDNESS

(71) Applicant: XYON HEALTH INC., Vancouver (CA)

(72) Inventors: Victor Hasson, Vancouver (CA); Mauro Castiglioni, Lentate Sul Seveso (IT)

(73) Assignee: XYON Health Inc., Vancouver (CA)

( * ) Notice: Subject to any disclaimer, the term of this patent is extended or adjusted under 35 U.S.C. 154(b) by 0 days.

(21) Appl. No.: 16/759,674

(22) PCT Filed: Oct. 26, 2018

(86) PCT No.: PCT/US2018/057861
§ 371 (c)(1),
(2) Date: Apr. 27, 2020

(87) PCT Pub. No.: WO2019/084503
PCT Pub. Date: May 2, 2019

(65) Prior Publication Data
US 2020/0383916 A1 Dec. 10, 2020

Related U.S. Application Data

(60) Provisional application No. 62/577,869, filed on Oct. 27, 2017.

(51) Int. Cl.
*A61Q 19/00* (2006.01)
*A61Q 7/00* (2006.01)
*A61K 8/25* (2006.01)
*A61K 8/04* (2006.01)
*A61K 8/00* (2006.01)
*A61K 8/89* (2006.01)
*A61K 8/14* (2006.01)
*A61P 17/00* (2006.01)
*A61P 17/14* (2006.01)
*A61K 9/127* (2006.01)
*A61K 9/06* (2006.01)
*A61K 31/58* (2006.01)
*A61K 47/10* (2017.01)
*A61K 47/22* (2006.01)
*A61K 47/24* (2006.01)
*A61K 47/32* (2006.01)
*A61K 47/34* (2017.01)
*A61K 9/00* (2006.01)
*A61K 45/06* (2006.01)

(52) U.S. Cl.
CPC .............. *A61K 9/127* (2013.01); *A61K 9/06* (2013.01); *A61K 31/58* (2013.01); *A61K 47/10* (2013.01); *A61K 47/22* (2013.01); *A61K 47/24* (2013.01); *A61K 47/32* (2013.01); *A61K 47/34* (2013.01); *A61P 17/14* (2018.01); *A61K 9/0014* (2013.01); *A61K 45/06* (2013.01)

(58) Field of Classification Search
CPC ........ A61K 9/0014; A61K 9/127; A61K 8/14; A61K 8/042; A61K 2300/00; A61K 8/11; A61K 8/553; A61K 2800/56; A61K 8/25; A61K 2800/10; A61K 8/044; A61K 8/585; A61P 17/14; A61P 17/00; A61Q 7/00; A61Q 19/00; A61Q 5/02; A61Q 5/002
See application file for complete search history.

(56) References Cited

U.S. PATENT DOCUMENTS

| | | | | |
|---|---|---|---|---|
| 5,498,420 A | * | 3/1996 | Mentrup Edgar | A61K 8/14 424/401 |
| 6,663,885 B1 | * | 12/2003 | Hager | A61K 8/14 424/450 |
| 2008/0118537 A1 | * | 5/2008 | Wang | A61K 8/891 424/401 |
| 2010/0048598 A1 | | 2/2010 | Kandavilli et al. | |
| 2010/0080768 A1 | | 4/2010 | McGraw et al. | |
| 2011/0081402 A1 | * | 4/2011 | Kojima | A61K 8/65 424/450 |
| 2011/0212167 A1 | * | 9/2011 | Ali | A61K 9/08 424/450 |
| 2011/0236499 A1 | * | 9/2011 | Billis | A61K 8/345 424/520 |
| 2013/0028950 A1 | | 1/2013 | Nishida et al. | |

FOREIGN PATENT DOCUMENTS

| | | | | |
|---|---|---|---|---|
| CN | 106361703 A | | 2/2017 | |
| EP | 0319638 A1 | * | 6/1989 | ............... A61K 8/68 |

(Continued)

OTHER PUBLICATIONS

Itoh M. (2014) Polyhedral Oligomeric Silsesquioxanes (POSS). In: Kobayashi S., Müllen K. (eds) Encyclopedia of Polymeric Nanomaterials. Springer, Berlin, Heidelberg. https://doi.org/10.1007/978-3-642-36199-9_220-1 (Year: 2014).*
Pierre, M.B.R., dos Santos Miranda Costa, I. Liposomal systems as drug delivery vehicles for dermal and transdermal applications. Arch Dermatol Res 303, 607 (2011). https://doi.org/10.1007/s00403-011-1166-4 (Year: 2011).*
Declaration of Dr. James J. Wang, filed on Aug. 19, 2010 in U.S. Appl. No. 11/603,269.
FDA label for Propecia® (rev. Jan. 2014).
Kim, M-K et al., Targeted and sustained delivery of hydrocortisone to normal and stratum corneum-removed skin without enhanced skin absorption using a liposome gel. J. Controlled Release 46:243-251 (1997).

(Continued)

*Primary Examiner* — Tracy Liu
(74) *Attorney, Agent, or Firm* — Wolf, Greenfield & Sacks, P.C.

(57) ABSTRACT

The present invention provides a liposomal topical formulation or a liposomal topical formulation base having barrier-forming siliconic components, methods for making the same, and methods for using the same in the treatment of dermatological diseases and conditions, including male pattern baldness.

30 Claims, 5 Drawing Sheets

(56) References Cited

FOREIGN PATENT DOCUMENTS

KR  10-2014-0080955 A   7/2014
WO  WO 98/25623 A1     6/1998

OTHER PUBLICATIONS

El Maghraby, GM et al., Liposomes and skin: From drug delivery to model membranes. Eur. J. Pharm. Sci. 34:203-222 (2008).
Extended European Search Report, dated Feb. 16, 2022 for European Application No. 21188525.6.
International Search Report and Written Opinion, dated Jan. 22, 2019 for International Application No. PCT/US2018/057861.
International Preliminary Report on Patentability, dated May 7, 2020 for International Application No. PCT/US2018/057861.
Castiglioni, M., Evaluation of Finasteride Gel Liposomial 2.5%. Farmacia Parati Lentate sul Seveso, Italy. (2015) 34 pages.
Castiglioni, M., Poster Presentation: Evaluation of Finasteride Gel Liposomial 2.5%. Farmacia Parati Lentate sul Seveso, Italy. (Jun. 26, 2015) Photograph. 1 page.
Kim et al., Combined Skin Moisturization of Liposomal Serine Incorporated in Hydrogels Prepared with Carbopol ETD 2020, Rhesperse RM 100 and Hyaluronic Acid. Korean J Physiol Pharmacol. (Nov. 2015) 19(6):543-547. doi: 10.4196/kjpp.2015.19.6.543.

\* cited by examiner

TOPICAL FORMULATIONS FOR TREATING DERMATOLOGICAL DISORDERS INCLUDING MALE PATTERN BALDNESS

1. REFERENCE TO RELATED APPLICATION

This application claims the benefit of U.S. Provisional Patent Application No. 62/577,869, filed on Oct. 27, 2017, the entire disclosure of which is hereby incorporated by reference in its entirety.

2. BACKGROUND

2.1. Technical Field

The present invention relates, in general, to formulations for treating dermatological diseases and disorders, methods of making such formulations, and methods of treatment using such formulations.

2.2. Description of the Related Art

Pattern hair loss in both men and women can be androgenic. It is generally believed that male sex hormones play a major role in the health of hair follicles. Hair follicles contain androgen receptors that bind with androgens; the resulting complexes could cause miniaturization of hair follicles and reduce nutrients being supplied to hair shafts.

As such, anti-androgens can be useful for management of hair loss. For instance, finasteride is the active ingredient in an oral formulation (marketed under the brand name Propecia®) for treating male pattern baldness. Finasteride's mechanism of action is inhibition of 5-α-reductase, the enzyme that converts testosterone into a more potent androgen, dihydrotestosterone (DHT). Oral finasteride can effectively lower DHT levels in scalp, which can arrest the progression of hair loss or promote new hair growth.

Although oral finasteride can be used to effectively treat hair loss in men, it is associated with a number of significant undesirable systemic side effects, which in turn can lead to poor patient compliance. For example, use of oral finasteride has been linked to low libido, erectile dysfunction, decreased arousal and problems with orgasm. See, e.g., Irwig, M. S., Kolukula, S. *J. Sex. Med.* 8(6), 1747-53 (2011). Generally, suppression of serum DHT is a marker for these and other undesirable side effects.

Based on early studies of finasteride, the occurrence of sexual dysfunction side-effects among finasteride users was thought to be around 2%, and appeared to reverse upon discontinuation of the drug. Over the past 10 years, however, accumulated evidence suggests the occurrence of erectile dysfunction among users is much higher than the 2% revealed in earlier studies. In addition, there has been evidence of permanent erectile dysfunction in certain individuals, a condition known as "post-finasteride syndrome" (PFS).

Some topical compositions containing finasteride are known in the art. For example, a topical solution formulation (known as P-3074) containing 0.25% w/w finasteride and employing hydroxypropyl chitosan (HPCH) film-forming technology has been reported (Caserini et al. *International Journal of Clinical Pharmacology and Therapeutics*, 2016, 54:19-27). However, P-3074 was found to lower serum DHT in a strongly dose-dependent manner. At some doses, P-3074 suppressed serum DHT (when measured against a pre-treatment baseline) to an extent equal to (or in some cases, exceeding) that observed with conventional oral finasteride therapy. Moreover, it is unclear what dose of P-3074 is required to effectively treat androgenic alopecia.

Accordingly, a need exists in the art for a composition that can deliver active pharmaceutical ingredients (APIs) topically to the skin while minimizing serum uptake of the same. Moreover, such topical compositions would pose (when compared to either compositions of the API intended for oral administration or topical compositions for transdermal drug delivery) a reduced theoretical safety risk in view of the resultant minimized systemic exposure.

3. BRIEF SUMMARY

Disclosed herein are pharmaceutical formulations for topical dermatological use. The formulations are particularly suited as a local depot for sustained and/or slow release of an active pharmaceutical ingredient (API), in particular, a dermally active agent.

The topical formulations described herein are particularly suitable for treating male-pattern baldness. Although androgen receptors are present on scalp in general, they are at higher concentrations on balding scalp (e.g., in smaller follicles) than on non-balding scalp. Thus, highly localized delivery of 5-α-reductase inhibitors to the balding scalp can be effective in arresting, delaying or reversing hair loss. The topical formulations described herein provide a "depot" effect by which the 5-α-reductase inhibitors are largely retained in the outer layers of the skin, e.g., epidermis and part of the dermis, which are not as well-vascularized as the deeper parts of the skin, resulting in significantly lower serum concentrations of the α-reductase inhibitors when compared with oral treatment or known topical treatments having the same inhibitors. In turn, the lower serum concentrations of the α-reductase inhibitors are correlated with reduced serum DHT suppression (i.e., higher serum DHT concentrations). Given the association of serum DHT suppression with a number of adverse effects (e.g., sexual dysfunction), these topical formulations offer a more favorable risk-benefit profile when compared to the corresponding oral formulations.

One embodiment provides a liposomal topical formulation base comprising: a plurality of liposomes; and an aqueous gel matrix in which the plurality of liposomes are dispersed, wherein the aqueous gel matrix comprises a gelling agent, a water-soluble silicone compound, a film forming agent, and water. Examples of film forming agents include polyacrylamides, polyacrylates, poly(vinyl)pyrrolidones, and co-polymers of these, and polysilsesquioxane compounds, preferably a poly(alkylsilsesquioxane) and most preferably poly(methylsilsesquinoxane). The base can be supplied to a user, e.g. a compounding pharmacy, for addition of one or more active pharmaceutical ingredients (API).

Thus, an embodiment of the invention provides a liposomal topical formulation comprising: a plurality of liposomes; one or more active pharmaceutical ingredients (API); and an aqueous gel matrix in which the plurality of liposomes are dispersed, wherein the aqueous gel matrix comprises a gelling agent, a water-soluble silicone compound, a film forming agent, and water. Examples of film forming agents include polyacrylamides, polyacrylates, poly(vinyl)pyrrolidones, and co-polymers of these, and polysilsesquioxane compounds, preferably a poly(alkylsilsesquioxane) and most preferably poly(methylsilsesquinoxane). In various embodiments, the API is a 5-α-reductase inhibitor. In more specific embodiments, the API is finasteride or dutasteride.

One embodiment provides a liposomal topical formulation comprising: a plurality of liposomes; at least one 5-α-reductase inhibitor, and an aqueous gel matrix in which the plurality of liposomes are dispersed, wherein the aqueous gel matrix comprises a gelling agent, a water-soluble silicone compound, and water. In specific embodiments, the at least one 5-α-reductase inhibitor comprises finasteride or dutasteride. In a preferred embodiment, the aqueous gel matrix further comprises a film forming agent. Examples of film forming agents include polyacrylamides, polyacrylates, poly(vinyl)pyrrolidones, and co-polymers of these, and polysilsesquioxane compounds, preferably a poly(alkylsilsesquioxane) and most preferably poly(methylsilsesquinoxane).

One embodiment provides a method for treating or preventing a dermatological disorder such as male pattern baldness, the method comprising administering the liposomal topical formulation according to the various embodiments disclosed herein.

Certain other embodiments provide compositions that have utility over a broad range of therapeutic applications, and may be used to treat diseases, such as androgenic alopecia (male pattern baldness), fungal infections, bacterial infections, acne, eczema, psoriasis, rosacea, vitiligo and inflammation. Accordingly, another embodiment provides methods for treating or preventing a dermatological disease or condition, the method comprising administering to a patient in need of such a treatment a therapeutically effective amount of a composition disclosed herein.

4. BRIEF DESCRIPTION OF THE FIGURES

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

Figure 5A:
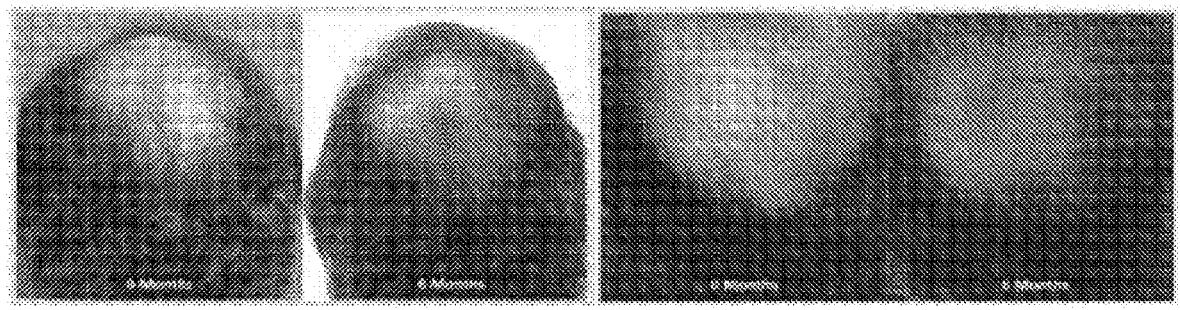
Figure 5B:
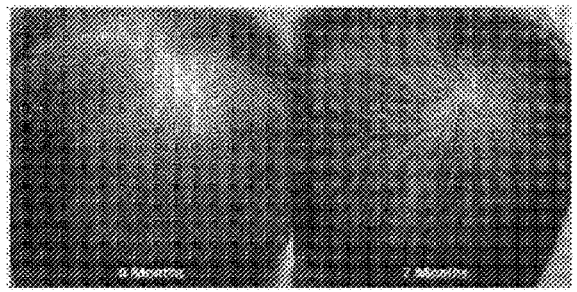
Figure 5C:
Figure 5D:
Figure 5E:
Figure 5F:
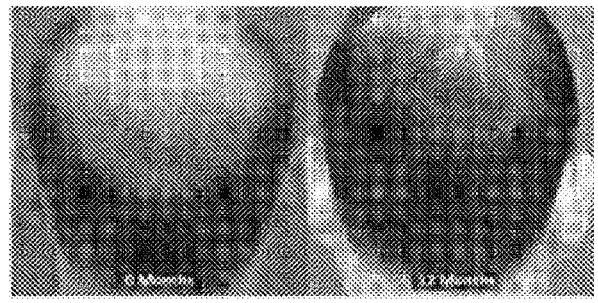
Figure 5G:
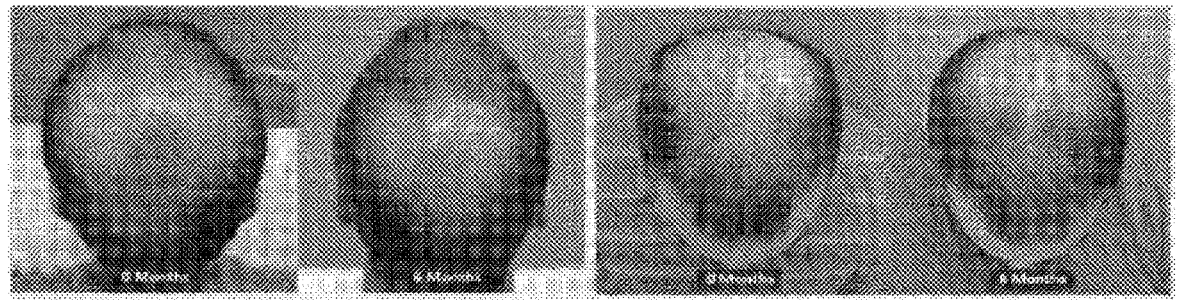
Figure 5H:
Figure 5I:
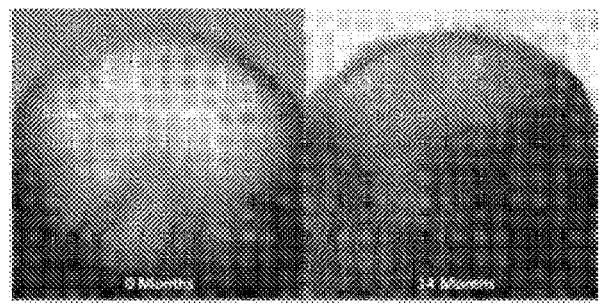

FIG. 5A-I depict scalp hair growth in subjects before and following topical administration of a finasteride formulation (2.5% w/w) according to an embodiment of this disclosure. More specifically, FIG. 5A depicts a subject at 0 months and after 6 months of treatment. FIG. 5B depicts a subject at 0 months and after 7 months of treatment. FIG. 5C depicts a subject at 0 months and after 13 months of treatment. FIG. 5D depicts a subject at 0 months and after 24 months of treatment. FIG. 5E depicts a subject at 0 months and after 6 months of treatment. FIG. 5F depicts a subject at 0 months and after 12 months of treatment. FIG. 5G depicts a subject at 0 months and after 6 months of treatment. FIG. 5H depicts a subject at 0 months and after 6 months of treatment. FIG. 5I depicts a subject at 0 months and after 14 months of treatment.

5. DETAILED DESCRIPTION

Disclosed herein are liposomal topical formulations capable of highly-localized, slow release of one or more APIs. Advantageously, due to a local depot effect and barrier function provided by the siliconic components of the formulations disclosed herein, the API penetrates through the stratum corneum of the epidermis and is largely confined to the epidermis and dermis. As a result, while a therapeutically effective local (skin) concentration of the API can be maintained; systemic exposure of the API is minimized. As a result, the liposomal topical formulations provide a therapeutic effect while reducing or eliminating side effects associated with systemic exposure, such as erectile dysfunction, sexual dysfunction and the like.

In various embodiments, the liposomal topical formulations disclosed herein may be loaded with one or more API(s) at suitable strengths; or may act as a base into which one or more API(s) could be added.

One embodiment thus provides an API-loaded liposomal topical formulation comprising an API, a plurality of liposomes entrapping the API, an aqueous gel matrix in which the plurality of liposomes are dispersed, wherein the aqueous gel matrix comprises a gelling agent, a water-soluble silicone compound, a film forming agent such as a polysilsesquioxane compound, and water.

Another embodiment provides a liposomal topical base formulation comprising a plurality of liposomes; an aqueous gel matrix in which the plurality of liposomes are dispersed, wherein the aqueous gel matrix comprises a gelling agent, a water-soluble silicone compound, a film forming agent such as a polysilsesquioxane compound, and water.

Optional additives may be present in the topical formulations disclosed herein. These additives serve as solvents, co-solvents, humectants, viscosity modifiers, antioxidants, stabilizers, penetration enhancers and the like.

The topical formulations, whether or not loaded with an API, have the consistency and spreadability of a gel or lotion. The topical formulations may also be in the forms of cream, spray, foam, serum, and the like.

These and other optional additives are described in further detail below.

5.1. Liposomes

Liposomes are small vesicles comprising amphiphilic lipids arranged in bilayers. Liposomes may contain several concentric lipid bilayers separated by aqueous channels (multilamellar vesicles or MLVs), or alternatively, they may contain a single membrane bilayer (unilamellar vesicles), which may be small unilamellar vesicles (SUVs) or large unilamellar vesicles (LUVs).

The vesicle-forming amphiphilic lipids are preferably ones having two hydrocarbon chains, typically acyl chains, and a polar head group. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 12-40, or more typically 14-22 carbon atoms in length. The hydrocarbon chains may contain varying degrees of unsaturation (i.e., 0 to up to 6 double bonds). The two hydrocarbon chains (or fatty chains) are covalently linked to a polar head group, which typically comprises an ionized moiety such as phosphate or ammonium. The above-described lipids and phospholipids can be obtained commercially or prepared according to known methods in the art. Other suitable lipids include glycolipids and sterols such as cholesterol.

In a preferred embodiment, the vesicle-forming lipid is lecithin, an amphiphilic compound typically derived from animal and plant tissues (e.g., egg yolks or soya beans). In general, lecithin includes a diglyceride of two fatty acids such as stearic, palmitic, and oleic acids. The diglyceride is coupled (via the third hydroxyl group) to a phosphoric acid, which incorporates a choline moiety. The lipids of the lecithin group are also commonly called phosphatidylcholines. Lecithin can be hydrogenated in a controlled manner to yield hydrogenated lecithin. In some embodiments, the lecithin is a hydrogenated lecithin, for example, Lecinol S-10 (Nikkol Group, Nikko Chemical Co., Ltd.).

In an aqueous medium, the amphiphilic lipid molecules spontaneously arrange into vesicles having a bilayer membrane defining an aqueous interior compartment. Composed of two lipid monolayers, the bilayer membrane has a hydrophobic region wherein the tails of the two lipid monolayers orient toward the center of the bilayer and a hydrophilic region wherein the heads of the lipid monolayer orients toward the aqueous interior of the vesicles and the aqueous medium in which the liposomes are dispersed.

The amount of the vesicle-forming lipid in an aqueous medium must reach a critical concentration to form stable liposomes. Typically, lecithin may be present in an amount of 0.1-5% (w/w) by the total weight of the topical formulation. More typically, the amount may be in the range of 0.1-4%, 0.1-3%, 0.1-2%, 0.1-1% and 0.5-1% and the like.

5.2. Active Pharmaceutical Ingredient (API)

Liposomes are capable of solubilizing both water-soluble and lipid-soluble compounds, making them effective carriers of APIs. For a given API, depending on its solubility in water or lipid, it may be trapped in the aqueous interior compartment, the lipid bilayer, or both according to a partition coefficient. Polar APIs (e.g., salts) are hydrophilic and are largely trapped in the aqueous compartment; whereas non-polar APIs are largely trapped in the lipid bilayer.

Liposomes are dynamic structures. The entrapped API, whether within the aqueous interior or the lipid bilayer, can be released in a slow or controlled manner.

In various embodiments, suitable APIs are topically active agents that treat or reduce the symptoms of various dermatological disorders. Examples of the APIs include, without limitation, an antifungal agent, an antibiotic, an anti-hypertensive vasodilator, a steroid, an anti-acne agent, a topical anti-inflammatory agent, or combinations thereof.

In a preferred embodiment, the API is a 5-α-reductase inhibitor. 5-α-Reductase has three isoforms, all involved in converting testosterone to dihydrotestosterone (DHT). Inhibitors of 5-α-reductase are therefore effective at reducing scalp DHT levels and arresting hair loss.

In some embodiments, the 5-α-reductase inhibitors are 4-azasteroid compounds such as finasteride, dutasteride and epristeride. These steroid compounds are highly lipophilic and can be efficiently trapped in the lipid bilayers of liposomes of the topical formulations disclosed herein and released in a highly localized manner.

Finasteride (structure shown below) selectively inhibits Type II and Type III 5-α-reductase, typically reducing serum DHT levels by about 65-70% after sustained oral administration. Because finasteride does not inhibit Type I 5-α-reductase, it does not fully suppress DHT production.

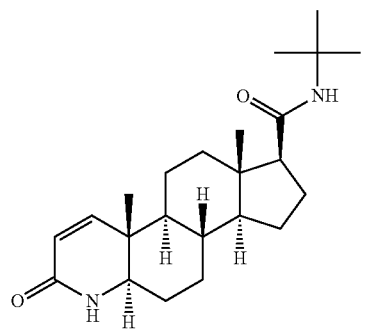

Dutasteride (structure shown below) inhibits all three 5-α-reductase isoforms and is capable of suppressing up to 99% of DHT production after sustained oral administration.

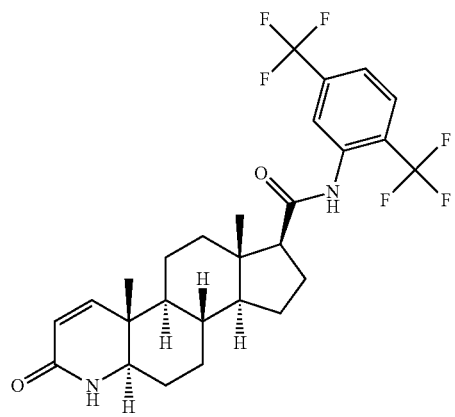

Other embodiments provide non-steroidal 5-α-reductase inhibitors. These compounds are not technically steroids; however, they also have fused or non-fused cyclic structures and are considered structural analogs of certain azasteroids. Suitable compounds include benzo[c]quinolizinones (e.g., bexlosteride), benzo[f]quinolonones, piperidones and the like.

In further embodiments, the API is saw palmetto extract, melatonin, or both saw palmetto extract and melatonin.

In yet other specific embodiments, the APIs may be dermatologically active agents that target infections, acne, pigmentation, premature aging and the like. Without limitation, examples of such APIs include psoralens, macrolides, retinoids, azole-based antifungal agents, allylamines, morpholino-based antifungal agents, selenium-based antifungal agents, hydroquinones, potassium channel openers, tetracyclines, minoxidil or combinations thereof.

"Antibiotic" or "antibiotic agent" refers to compounds or a combinations of compounds that are destructive to or inhibit the growth of microorganisms including bacteria, protozoa and/or microbes. As used herein, the term "antibiotic" includes antibacterial agents, antimicrobial agents, and the like. Examples of antibiotic agents include, but are not limited to, penicillins, cephalosporins, polymyxins, rifamycins, lipiamycins, quinolones, sulfonamides, macrolides, lincosamides, tetracyclines, cyclic lipopeptides, glycylcyclines, oxazolidinones, and lipimycins.

"Antifungal" or "fungicide" refers to compounds or combinations of compounds that treat or prevent mycoses (i.e., kill or inhibit the growth of fungi). Antifungals include, but are not limited to, polyenes (e.g., amphotericin B, candicidin, filipin, hamycin, natamycin, nystatin, rimocidin), imidazoles (e.g., bifonazole, butoconazole, clotrimazole, econazole, fenticonazole, isoconazole, ketoconazole, luliconazole, miconazole, omoconazole, oxiconazole, sertaconazole, sulconazole, tioconazole), triazoles (e.g., albaconazole, efinaconazole, epoxiconazole, fluconazole, isavuconazole, itraconazole, posaconazole, propiconazole, ravuconazole, terconazole, voriconazole), thiazoles (e.g., abafungin), allylamines (e.g., amorolfin, butenafine, naftifine, terbinafine), echinocandins (e.g., anidulafungin, caspofungin, micafungin), aurones, benzoic acid, ciclopirox, flucytosine, griseofulvin, haloprogin, tolnaftate, undecylenic acid, crystal violet, and Balsam of Peru.

It is noted that suitable APIs for the present disclosure are not limited to the above specific examples. Rather, the liposomal topical formulation disclosed herein can be loaded with any API.

The API may be loaded at a suitable amount depending on its efficacy, at strengths suitable for the treatment or prophylaxis of a particular disorder. A 5-α-reductase inhibitor may be loaded at about 0.5-5% (w/w) of the total weight of the topical formulation. More preferably the amount is in the range of 0.5-4%, 0.5-3%, 1-4%, 1-3%, 2-5%, 2.5-4%, 4-5% and the like. In preferred embodiments, finasteride or dutasteride is present at 2.5% (w/w) of the total weight of the topical formulation.

5.3. Gelling Agent

A gelling agent is a hydrophilic polymer that is insoluble in water, but can absorb water and swell into up to 1000 times its original volume. The gelling agent, having absorbed water and having swollen into a gel, provides a matrix in which the liposomes can be uniformly dispersed.

Suitable gelling agents include, for example, acacia, alginic acid, bentonite, Carbopols (now known as carbomers), cellulose-based polymers, gelatin, poloxamers (Pluronics), polyvinyl alcohol, sodium alginate, tragacanth, and xanthan gum.

In a preferred embodiment, the gelling agent is a carbomer, which refers to a class of polymers of acrylic acid or acrylate (esters of acrylic acid) crosslinked by for example, divinyl glycol and polyalkenyl ethers. Carbomers readily absorb water without dissolving in water. The crosslinked structure allows the polymer to swell and form a gel-like consistency. Examples of polyacrylate polymers include, without limitation, polyacrylonitrile, polyacrylic acid and alkyl acrylate cross polymers. Polyacrylate polymers also include, but are not limited to, polyacrylic acid, polymethacrylic acid, polymethyl methacrylate, poly butylacrylate, poly 2-ethylhexyl acrylate or poly($C_{10}$-$C_{30}$ alkyl acrylate) cross polymers. In certain embodiments, the acrylate polymer comprises a $C_{10}$-$C_{30}$ alkyl acrylate cross polymer, for example, Carbopol Ultrez® 21 (Lubrizol Advanced Materials, Inc.).

In other embodiments, cellulose-based polymers such as carboxymethyl cellulose, ethylcellulose, hydroxyethyl cellulose, hydroxypropyl cellulose, methylcellulose are used as gelling agents.

Gelling agents are used at concentrations of 0.5% to 10% by weight, depending on the agent and the target viscosity of the formulation. For carbomers (e.g., Carbopol Ultrez® 21), the amount by weight of the total topical formulation is about 0.1-5%. More typically the amount is in the range of 0.5-4%, 0.1-4%, 0.1-3%, 0.5-2%, 0.5-1% and the like. In preferred embodiments, the carbomer may be present at 0.8% (w/w) of the total weight of the topical formulation.

5.4. Water-Soluble Silicone Compounds

Silicone, also known to as polysiloxane, is a class of organosilicon polymer having a plurality of silicon-carbon bonds and siloxane linkages (—Si—O—Si—) in the polymer backbone. Polysiloxane is typically a linear polymer but may be modified to contain branches or pendants of other chemical moieties or polymers.

The most common silicone is poly(dimethylsilloxane), or PDMS or dimethione, which has the following structure:

wherein n is an integer and the number of n determines the molecular weight, viscosity, density of the polydimethylsiloxane.

Unmodified PDMS is highly hydrophobic and not compatible with an aqueous-based formulation. However, PDMS (or other polysiloxanes) can be modified to contain hydrophilic pendants or capping groups. Such hydrophilic groups include, for example, polyols such as polyethylene glycol (PEG) and polypropylene glycol (PPG). Examples of modified, water-soluble silicones include PEG-modified silicones or PPG-modified silicones.

The PEG or PPG moieties may be appended to any one or more of the repeating units by replacing one or more methyl groups or coupling to a modified methyl group having reactive groups such as hydroxyl. The PEG or PPG moieties may also replace the one or both of the end methyl group of PDMS. As the number of the ethylene oxide or propylene oxide units appended to the PDMS chain increases, the hydrophilicity increases and the modified PDMS becomes more and more water-soluble. Hydrophilicity can be measured by the hydrophile-lipophile balance (HLB) number. As used herein, the term "water-soluble silicone compound" refers to a silicone having a HLB of at least 10.

As used herein, the molecular weight of the silicone portion of the water-soluble silicone compound is less than 10,000, and more preferably, less than 8,000, or less than 6,000. In various embodiments, n is in the range of 20-100, more preferably, 20-80, or still more preferably, 30-60.

In an embodiment, at least 6 ethylene oxide or propylene oxide units are present for each molecule of PDMS for the PEG or PPG-modified silicone to be appreciably water-soluble. More preferably, at least 8 ethylene oxide or propylene oxide units are present for each molecule of PDMS. In various embodiments, the water soluble silicone is represented by PEG-X silicone or PPG-X silicone, wherein x is an integer between 6 and 40, wherein x represents the number of ethylene oxide units. More preferably, x is 8-20, and still more preferably, x is 8-15.

In a preferred embodiment, the water-soluble silicone compound is PEG-8 dimethicone, for example Silwax® WS-4 (Siltech Corporation, Toronto, Ontario).

In other embodiments, the water-soluble silicone compound is Bis-PEG-18 methyl ether dimethylpolysiloxane, wherein the two capping groups of the polysiloxane chain are PEG-18 (18 units of ethylene oxide).

The water-soluble silicone compound is used at concentrations of 0.5-20% or more preferably 5-20% (w/w) of the total weight of the topical formulation. In various embodiments, the amount of the water-soluble silicone compound is in the range of 5-15%, or 5-10% or 8-15% or 8-10% and the like. In preferred embodiments, the PEG-8 dimethicone may be present at 10% (w/w) of the total weight of the topical formulation.

5.5. Film Forming Agents; Polysilsesquioxane Compounds

As used herein, "film forming agents" refers to polymers or co-polymers that contain a hydrophilic moiety in their repeating units. Examples of film forming agents include polyacrylamides, polyacrylates, poly(vinyl)pyrrolidones, and co-polymers of these. Polysilsesquioxane compounds are preferred film forming agents.

A polysilsesquioxane compound is a branched siloxane polymer having a chemical formula $[RSiO_{3/2}]_n$, wherein n is an integer greater than zero and R is H, alkyl, aryl, or alkoxy.

As used herein, n is typically an integer up to 100.

As used herein, "alkyl" refers to a straight or branched hydrocarbon chain radical consisting solely of carbon and hydrogen atoms, containing no unsaturation, having from one to twelve carbon atoms, and which is attached to the rest of the molecule by a single bond. Preferably, the alkyl radial has one to eight carbon atoms, more preferably one to six carbon atoms. Examples of alkyl radicals include methyl, ethyl, n-propyl, 1-methylethyl (iso-propyl), n-butyl, n-pentyl, 1,1-dimethylethyl (t-butyl), 3-methylhexyl, 2-methylhexyl, and the like.

As used herein, "aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene.

As used herein, "alkoxy" refers to a radical of the formula $-OR_a$ where $R_a$ is an alkyl radical as defined above containing one to twelve carbon atoms.

Polysilsesquioxane compounds generally adopt a cage-like or ladder-like structure with Si—O—Si linkages. In a preferred embodiment, the polysilsesquioxane compound is a poly(alkylsilsesquioxane). Still more preferably, the polysilsesquioxane compound is poly(methylsilsesquinoxane) (i.e., R is methyl), which is commercially available under the brand name Gransil PSQ® (Grand Industries, Inc., Elmwood Park, N.J.).

Polysilsesquioxane compounds are especially preferred film-forming polymers. When applied topically (including on the scalp), a polysilsesquioxane compound, alone or together with the water-soluble silicone, is capable of forming a barrier, thereby slowing down the penetration and diffusion of the API. It is believed that the polysilsesquioxane compound forms a 3D mesh structure when applied to the skin. The mesh structure serves to entrap the liposomes in a mask-like covering of the scalp. The API (e.g., finasteride) is released in a controlled fashion into the skin, where it is thereafter retained. Only very small amounts of finasteride are able to permeate entirely through the skin.

The polysilsesquioxane compound is present at concentrations of 1-20% (w/w) of the total weight of the topical formulation. In various embodiments, the amount of the polysilsesquioxane compound is in the range of 1-10%, or 5-10% or 1-5% or 10-20% and the like. In a preferred embodiment, the polysilsesquioxane compound is Gransil PSQ®. Still more preferably, the Gransil PSQ® is present at 5% (w/w) of the total weight of the topical formulation.

5.6. Optional Additives

Solvents and co-solvents suitable for the topical formulation include, without limitation, one or more alcohols, or isosorbide.

Alcoholic solvents can be any solvent having at least one hydroxyl group. Alcoholic solvents can be miscible with both water and organic substances (such as PEG-silicone and polysilsesquioxane). The alcoholic solvent may be, without limitation, propanediol, phenoxyethanol, aminomethyl propanol and the like.

The optional additive may further include isosorbide, which is a versatile solvent that is compatible with both water and organic solvents. Isosorbide refers to a compound having the following structure:

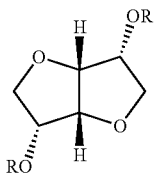

wherein R at each occurrence, independently H or $C_1$-$C_6$ alkyl. When at each occurrence R is methyl, the above compound is dimethyl disosorbide (or DMI), which is commercially available under the brand name Gransolve® DMI (Grant Industries, Elmwood Park, N.J.).

The optional additive may further include a humectant, which helps to reduce moisture loss after the topical application is applied. An example of a suitable class of humectant is glyceryl derivatives, which refers to compounds derived from glycerol (1,2,3-propanetriol), wherein one or more of the hydrogens of the hydroxyl groups of glycerol are replaced by a straight or branched alkyl, alkenyl, or alkynyl chain. Glyceryl derivatives include mono-, di- and tri-esters of glycerin, for example, glyceryl caprylate (caprylyl glycol), ethylhexylglycerin, and mixtures thereof. In some embodiments, the glyceryl derivative is caprylyl glycol, for example Neofect® 403 (IMCD N.V., Rotterdam, The Netherlands).

In other embodiments, the composition optionally includes one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other embodiments of the composition include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other embodiments of the composition include one or more antioxidants to enhance chemical stability where required. Suitable antioxidants include, by way of example only, butylated hydroxytoluene, butylated hydroxyanisole, Vitamin E, ascorbic acid and sodium metabisulfite.

5.7. Method of Making the Topical Formulation

The topical formulation of the present disclosure can be made sequentially by first forming the liposomes and then the gel matrix. Vesicle-forming lipids are mixed with water while stirring, whereby the lipids form into liposomes under the shear force of the mixing. To this mixture, a gelling agent, water-soluble silicone compound and, if desired, a polysilsesquioxane compound can be added under stirring, until a homogeneous and uniform formulation is formed.

Additional optional additives can be added at any point of the process, preferably after the liposome formation.

As discussed herein, a liposomal topical base formulation may be formed without the API. The base formulation takes the form and consistency of a gel and thereafter can be loaded with one or more API(s).

Alternatively, the API is loaded during the formation of the liposome or after the formation of the liposome but before the formation of the gel matrix (i.e., before adding a gelling agent).

The silicone components, including water-soluble silicone compound and, if present, a polysilsesquioxane compound may be added to the liposomes (with or without API). These silicone components are film-forming compounds and contribute to the depot effect of the API release from the topical formulation.

5.8. Use of the Topical Formulation

The topical formulation disclosed herein may be applied to the skin, including scalp, of a subject. "Subject" refers to an animal, such as a mammal, for example a human. The methods described herein can be useful for both human therapeutics and veterinary applications. In some embodiments, the subject is a mammal, and in some embodiments, the subject is human.

As discussed herein, due to the depot effect, the API may be released slowly and in a highly localized manner. In particular, as demonstrated in the Examples in which finasteride-loaded topical formulations were tested for skin permeation and retention, it was observed that the formulation according to the present disclosure resulted in steady state plasma concentration at about 1.5- to 5.5-fold less than known topical formulations with no siliconic components. It was also observed that the flux and amount of finasteride that permeated the skin may be greatly reduced for formulations prepared according to embodiments of the present disclosure.

In some embodiments, the composition is administered in multiple doses. In some embodiments, dosing is about once, twice, three times, four times, five times, six times, or more than six times per day. In other embodiments, dosing is about once a month, once every two weeks, once a week, or once every other day. In yet another embodiment, the administration continues for more than about 6, 10, 14, 28 days, two months, six months, or one year. In some cases, continuous dosing is achieved and maintained as long as necessary. For example, in one embodiment, a composition of any one of the foregoing embodiments is administered once per day for 3 weeks.

Administration of the composition may continue as long as necessary. In some embodiments, a composition is administered for more than 1, 2, 3, 4, 5, 6, 7, 14, or 28 days. In some embodiments, a composition is administered chronically on an ongoing basis, e.g., for the treatment or prophylaxis of chronic conditions.

Dermatological conditions or disorders that may be addressed or treated by the topical formulations include, without limitation, androgenic alopecia (male pattern baldness), infection (a bacterial or fungal infection), acne, eczema, psoriasis, rosacea, vitiligo, inflammation, pain, itch and the like. More specifically, such diseases and symptoms may include by way of example and not limitation, a cutaneous condition, skin cancer, mycosis, dermatitis, a blister, scabies, a skin infection (e.g., fungal, bacterial or other microbial), allergic reaction, erythema, skin ulcer, contact dermatitis, seborrheic dermatitis, skin infection, acne, atopic dermatitis, melanoma, warts, vitiligo, psoriasis, skin rash, hives, pustule, herpes simplex, ringworm, autoimmune disease, xeroderma, lupus erythematosus, impetigo, keratosis, basal-cell carcinoma, squamous cell skin cancer, nodules, rosacea, hyperpigmentation, burns (e.g., first degree, second degree, third degree, sunburns), cysts, lichen planus, skin puncture or cut (i.e., wounds), shingles, bullous pemphigoid, ichthyosis, molluscum contagiosum, athlete's foot, alopecia areata, folliculitis, cellulitis, pemphigus, pityriasis, and candidiasis.

6. EXAMPLES

Example 1: Preparation of 2.5% w/w Finasteride Topical Composition

A sanitized turbo-emulsifier was charged with water, followed by Lecinol S-10. The resultant mixture was stirred at high speed for 10 minutes at ambient temperature. While maintaining stirring, the mixture was warmed to 70° C. and stirred for an additional 60 minutes at 70° C. Carbopol Ultrez® 21 was added and the resultant mixture was stirred at medium speed at 70° C. for 10 minutes and allowed to stand at a temperature of 70° C. for 30 minutes, ensuring the acrylate polymer was solvated. To the mixture was added a solution of finasteride in 1,3-propane diol and the resultant mixture was stirred at high speed for 10 minutes at 70° C. While maintaining stirring, the mixture was allowed to cool to 30° C. and Neofect® 403, phenoxyethanol, Silwax® WS, and dimethyl isosorbide were added sequentially. To the resultant homogeneous mixture was added 2-amino-2-methylpropan-1-ol followed by stirring at high speed for 10 minutes. Thereafter, Gransil PSQ® was added to the mixture, followed by 10 minutes of high speed stirring to afford a homogeneous gel. The final concentration of each respective component is shown in Table 1 below:

TABLE 1

Component concentrations for a 2.5% w/w finasteride topical composition

| Component (Commercial Name) | Concentration (% w/w) | INCI Name |
|---|---|---|
| Purified water | 59.9 | Aqua |
| Lecinol S-10 | 0.5 | Hydrogenated Lecithin |
| Carbopol Ultrez ® 21 | 0.8 | Acrylates/C 10-30 Alkyl Acrylate Crosspolymer |
| Finasteride | 2.5 | — |
| 1,3-propanediol | 10.0 | Propanediol |
| Neofect ® 403 | 0.8 | Caprylyl Glycol/Glyceryl Capprylate/Ethylhexyl glycerin |
| Phenoxyethanol | 0.2 | Phenoxyethanol |
| Silwax WS ® | 10.0 | PEG-8 Dimethicone |
| Gransolve ® DMI | 10.0 | Dimethyl Isosorbide |
| AMP | 0.3 | (aminomethyl)propanol |
| Gransil PSQ ® | 5.0 | Poly(methylsilsesquioxane) |

Example 2: Preparation of Gel Base

A sanitized turbo-emulsifier was charged with water, followed by Lecinol S-10. The resultant mixture was stirred at high speed for 10 minutes at ambient temperature. While maintaining stirring, the mixture was warmed to 70° C. and stirred for an additional 60 minutes at 70° C. Carbopol Ultrez® 21 was added and the resultant mixture was stirred at medium speed at 70° C. for 10 minutes and allowed to stand at a temperature of 70° C. for 30 minutes, to achieve solvation of the acrylate polymer. While maintaining stirring, the mixture was allowed to cool to 30° C. and Nefect® 403, phenoxyethanol, Silwax® WS, and dimethyl isosorbide were added sequentially. To the resultant homogeneous mixture was added 2-amino-2-methylpropan-1-ol followed by stirring at high speed for 10 minutes. Gransil PSQ® was added to the mixture, followed by 10 minutes of high speed stirring to afford a homogeneous gel. The final concentration of each respective component is shown in Table 2 below:

TABLE 2

Component concentrations of a representative gel base

| Component (Commercial Name) | Concentration (% w/w) | INCI Name |
| --- | --- | --- |
| Purified water | 72.4 | Aqua |
| Lecinol S-10 | 0.5 | Hydrogenated Lecithin |
| Carbopol Ultrez® 21 | 0.8 | Acrylates/C 10-30 Alkyl Acrylate Crosspolymer |
| Neofect® 403 | 0.8 | Caprylyl Glycol/Glyceryl Capprylate/Ethylhexyl glycerin |
| Phenoxyethanol | 0.2 | Phenoxyethanol |
| Silwax WS® | 10.0 | PEG-8 Dimethicone |
| Gransolve® DMI | 10.0 | Dimethyl Isosorbide |
| AMP | 0.3 | (aminomethyl)propanol |
| Gransil PSQ® | 5.0 | Poly(methylsilsesquioxane) |

Example 3: Preparation of 2.5 w/w Finasteride Topical Gel Via Compounding

A mixture of finasteride (2.5 g) and the liposomal gel base of Example 2 (2.5 g) was levigated (i.e., milled together) at ambient temperature in an electronic mortar and pestle (e.g., Unguator E/S, Galenova, Inc., Saint-Hyacinthe, QC, Canada) for 5 minutes. Additional liposomal gel base (95 g) was added portion-wise over 10 minutes and the levigation was continued until a visually-homogeneous mixture is obtained.

Pharmacokinetic Analysis of Subjects Dosed with 2.5% w/w Finasteride Topical Composition A pharmacokinetic (PK) and pharmacodynamic (PD) clinical study was performed to ascertain whether the topical liposomal formulation of Example 3 (i.e., a 2.5% w/w finasteride topical liposomal composition) leads to modest systemic exposure of finasteride in human subjects, and to determine whether daily application of the topical liposomal formulation of Example 1 to the scalp for three weeks leads to an attenuation of the reduction of plasma dihydrotestosterone (DHT) observed with conventional finasteride therapy.

Bioanalysis

Ultra-high performance liquid chromatography/tandem mass spectrometry (UPLC-MS/MS) assays for the quantitation of finasteride and DHT in human plasma were developed and qualified.

The assay for finasteride employed a stable isotope-labeled (deuterated) internal standard and was qualified over a linear range of 0.05 ng/mL (lower limit of quantitation) to 50 ng/mL (coefficient of determination=0.9985) using an 8-point calibration curve. The signal-to-noise ratio at the lower limit of quantitation was >10. Quality control (QC) standards were prepared using finasteride in blank human plasma at nominal concentrations of 0.2 ng/mL (low QC), 1 ng/mL (mid QC) and 40 ng/mL (high QC). The quality control standards were analyzed in quadruplicate and the concentration of finasteride interpolated from the linear calibration curve using peak area ratio methodology versus the internal standard. Each replicate calculated concentration was within ±13% of the nominal concentration for each of the low, mid and high QC standards. Blank samples were also injected at regular intervals in order to confirm the absence of analyte carry-over. The assay was therefore considered qualified for the accurate determination of finasteride in human plasma.

The assay for DHT employed a stable isotope-labeled (deuterated) internal standard and was qualified over a linear range of 50 pg/mL (lower limit of quantitation) to 10,000 pg/mL (coefficient of determination=0.9988) using an 8-point calibration curve. The signal-to-noise ratio at the lower limit of quantitation was >10. Quality control (QC) standards were prepared using DHT in blank human plasma at nominal concentrations of 50 pg/mL (low QC), 200 pg/mL (low-mid QC), 1,000 pg/mL (mid-high QC) and 8,000 pg/mL (high QC). The quality control standards were analyzed in quadruplicate and the concentration of DHT interpolated from the linear calibration curve using peak area ratio methodology versus the internal standard. Each replicate calculated concentration was within ±14% of the nominal concentration for each of the low, mid and high QC standards. Blank samples were also injected at regular intervals in order to confirm the absence of analyte carry-over. The assay was therefore considered qualified for the accurate determination of DHT in human plasma.

Study Design

In a controlled study, six male subjects not previously treated with finasteride, and one male subject previously treated with finasteride but who had discontinued finasteride therapy for the preceding seven days, were administered a pre-treatment blood draw to establish baseline levels of finasteride and DHT. No finasteride was detected in the previously untreated subjects; the previously treated subject had a baseline finasteride level of 0.098 ng/mL where the lower limit of detection was 0.05 ng/mL. The subjects were provided with the formulation of Example 3 and were instructed to apply it daily (as a thin layer) to the scalp for 20 consecutive days. The subjects were then instructed to return to the clinic on the day of their final dose (i.e., Day 21). After a pre-dose blood sample was taken, the subjects were administered their final (i.e., 21") dose. Blood samples were taken 1, 2, 4, 8 and 24 hours post-dose. The blood samples were processed to plasma and stored at −80° C. prior to UPLC/MS-MS analysis.

Assay Performance and Quality Control

A pharmacokinetic (PK) assay was developed to detect finasteride and dihydrotestosterone (DHT) concentrations in human serum, respectively. Assay performance was within standard acceptance criteria (i.e., linearity of calibration curve, recovery of standards, bias of QC samples across operating range, etc.). It was noted that Test Subject 1 had a pre-test finasteride serum concentration of 0.098 ng/mL (98 pg/mL), which was ascribed to inadequate pre-study wash-out. All other test subjects had finasteride concentrations below the lower limit of quantitation (i.e., <50 pg/mL) of the assay, which was expected for the pre-test samples.

Pharmacokinetic Analysis of 2.5% w/w Finasteride Topical Composition

Figure 1:
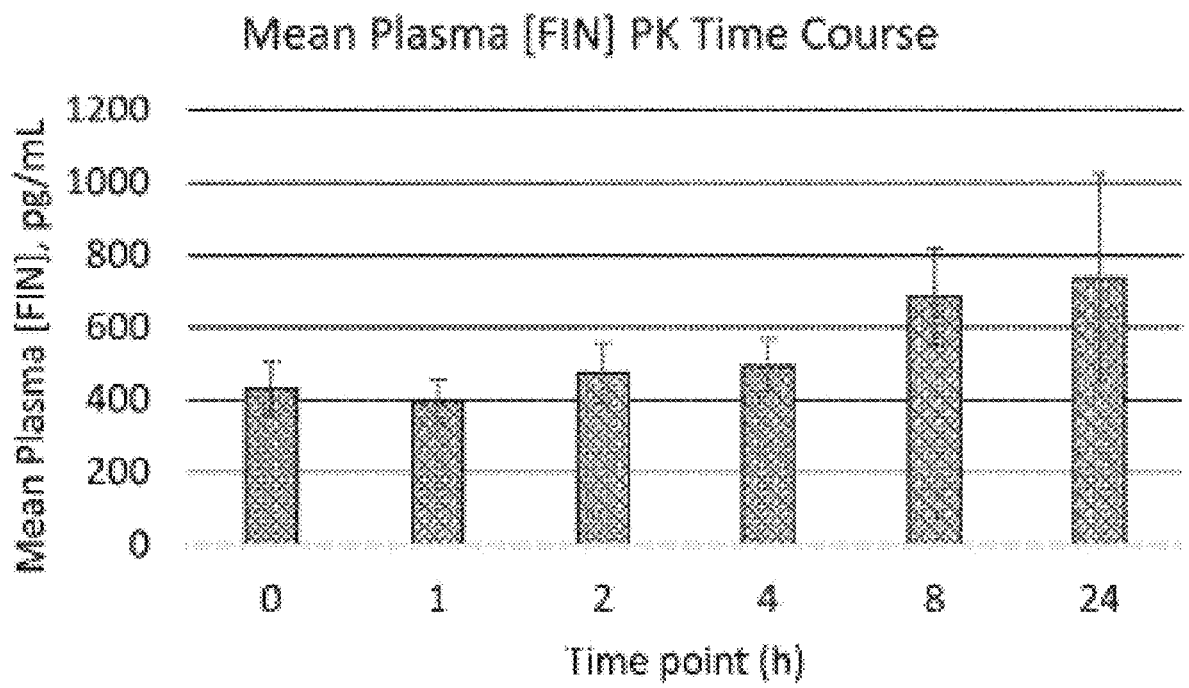
FIG. 1 illustrates the mean plasma concentration of finasteride at time points following topical administration of a 2.5% w/w composition of finasteride according to an embodiment of the present disclosure.

After dosing once per day for 3 weeks with the 2.5% w/w finasteride topical liposomal composition of Example 3, plasma levels were tested to determine the finasteride serum concentration. Results indicated that finasteride serum concentrations were consistent over the 24 hour PK monitoring interval (i.e., between about 4.31 ng/mL and 7.37 ng/mL) and showed no dramatic increase (i.e., "spike") post-dose. In contrast, oral formulations of finasteride typically show a dramatic increase in serum finasteride concentration following dosage. The stable serum concentration in the topical treatment indicates a slow and steady egress of finasteride from the skin into the plasma. These data reflect the "depot" or "anchor" effect of the composition when a 2.5% w/w finasteride topical liposomal composition is administered. That is, the concentration of finasteride on the skin remains highly localized and the therapeutic agent (i.e., finasteride) is released slowly while the finasteride serum concentration does not show a dramatic or substantial increase. The results of the time course study are shown below in Table 3 and in FIG. 1.

TABLE 3

Mean finasteride serum concentration over 24 hours at steady state

| Time Point (hours) | Concentration ± σ† (ng/mL) |
| --- | --- |
| 0 | 4.31 ± 2.82 |
| 1 | 3.97 ± 2.68 |
| 2 | 4.74 ± 2.75 |
| 4 | 4.95 ± 2.76 |
| 8 | 9.84 ± 3.46 |
| 24 | 7.37 ± 4.72 |

σ = standard deviation

The highest individual plasma concentration level detected was 13.90 ng/mL.

Pharmacodynamic Analysis of 2.5% w/w Finasteride Topical Composition

After 3 weeks of treatment as described above, a modest reduction in the concentration of dihydrotestosterone (DHT) in serum of 31%±21% (range: 0-53%) was observed. By way of comparison, typical reduction in DHT serum concentration for oral formulations range from 60 to 70%. That is, the present compositions show an approximately 2-fold less reduction of DHT serum concentration when compared with oral finasteride therapy.

Figure 2:
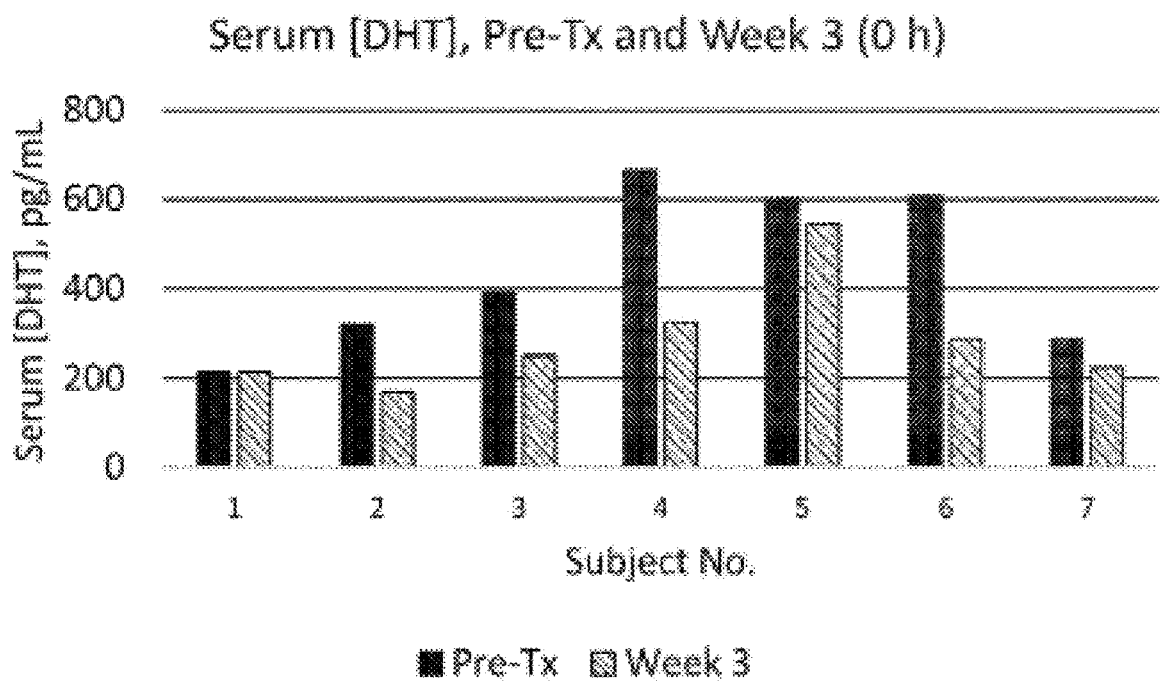
FIG. 2 shows a comparison of DHT serum concentration before treatment and at $T_0$ (i.e., pre-dose) of the 3rd week of treatment.

The results were obtained by comparing the pre-test DHT serum concentration to the DHT serum concentration at $T_0$ of the last treatment (i.e., week 3). The data are shown below in Table 4 and in FIG. 2.

TABLE 4

DHT serum concentrations pre-test and $T_0$ at week 3

| Test Subject | Pre-Test DHT Concentration (ng/mL) | Week 3 $T_0$ DHT Concentration (ng/mL) | Relative Decrease (%) |
| --- | --- | --- | --- |
| 1 | 2.14 | 2.14 | 0 |
| 2 | 3.20 | 1.69 | 47 |
| 3 | 3.91 | 2.49 | 36 |
| 4 | 6.65 | 3.25 | 51 |
| 5 | 6.02 | 5.45 | 9 |
| 6 | 6.08 | 2.87 | 53 |
| 7 | 2.87 | 2.25 | 22 |
| Mean | 4.41 | 2.87 | 31 |
| Standard Deviation (σ) | 1.80 | 1.24 | 21 |

Figure 3:
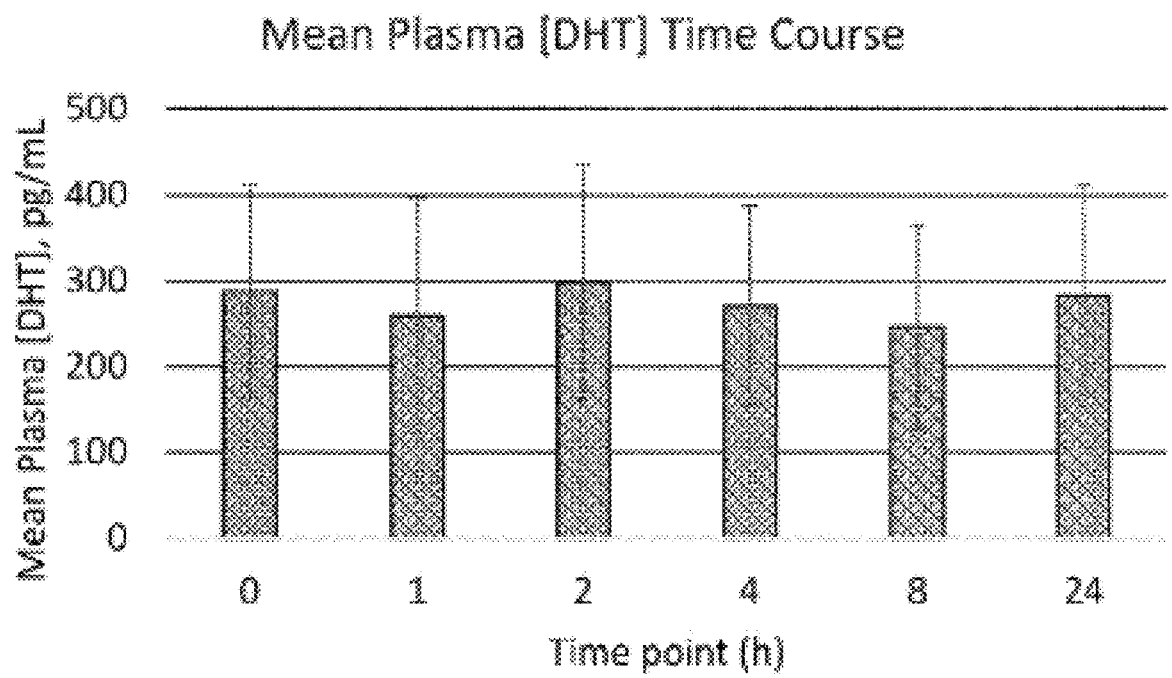
FIG. 3 shows the mean plasma concentration of DHT over a time course of 24 hours.

In addition, the time course mean DHT serum concentration was remarkably consistent over the 24 hour monitoring interval. The data show no sharp increase or drop in DHT serum concentration, which indicates slow, sustained release of the active therapeutic agent (i.e., finasteride). The results of the time course DHT serum concentration PD study are shown in Table 5 below and in FIG. 3.

TABLE 5

Mean DHT serum concentrations over 24 hours

| Time Point (hours) | Concentration ± σ† (ng/mL) |
| --- | --- |
| 0 | 2.87 ± 1.24 |
| 1 | 2.59 ± 1.37 |
| 2 | 2.98 ± 1.37 |
| 4 | 2.70 ± 1.16 |
| 8 | 2.46 ± 1.19 |
| 24 | 2.81 ± 1.30 |

Conclusions

The data demonstrate that the delivery of finasteride by the liposomal formulation of finasteride is largely restricted to the top layers of the skin. While slow, sustained release of finasteride into systemic circulation was observed, the plasma finasteride levels were generally very modest (in no cases exceeding 14 ng/mL). The mean reduction in plasma DHT by finasteride was far less pronounced with the composition of the liposomal formulation of finasteride (31%) than with oral finasteride therapy (60-70%). Therefore, the data shows that the liposomal formulation of finasteride effectively delivers finasteride to the skin with reduced systemic exposure and causes less reduction in systemic DHT levels than occurs with oral finasteride therapy.

Example 4: Stability Testing

The composition prepared according to Example 1 was subjected to stability testing Stability tests were performed to determine physical stability, accelerated and long-term physico-chemical stability, and the absence of microbial contamination. The formulation was exceptionally robust under the testing conditions for each test administered.

Physical Stability

The formulation was centrifuged for 5 hours. Upon recovery of the sample, no phase separation was observed, which indicated that the formulation was physically stable under rigorous physical conditions.

Accelerated and Long-Term Stability

The formulation was also subjected to accelerated and long-term stability testing. For accelerated stability tests, samples were held at 40° C. for 3 months. Long-term stability was tested by holding samples at 25° C. for 12 months. The samples were then observed for any changes in physical characteristics. Advantageously, the formulation showed excellent stability at the conclusion of each study, which demonstrates that embodiments of the formulations disclosed herein have outstanding stability.

Microbial Testing

The formulation was tested for contamination. At time points of 0, 1, 3, and 12 months samples were tested for yeast, molds, and bacteria. At each time point the composition showed no detectable signs of microbial contamination or microbial growth. Accordingly, embodiments of formulations disclosed herein can be stored for long periods while remaining free of any unwanted contaminants.

Example 5: In Vitro Skin Permeation Assessment of Dutasteride

To investigate the impact of the siliconic components in dutasteride-loaded formulations, in vitro tests were conducted to measure the permeation through and retention into skin epidermis of a dutasteride-loaded siliconic gel formulation made according to the same process of Example 1 (by replacing finasteride with dutasteride). As a comparison, a gel spray of dutasteride without silicone (PEG-8 Dimethicone or Poly(methylsilsesquioxane)) was also prepared. An original Franz-type diffusion cell system was modified to accommodate widened vertical columns and removal of the bowl shape. The diffusion area was 0.636 cm$^2$ with a receiver capacity of approximately 3.0 mL. The receiver volume for each cell was individually calibrated.

Skin Preparation

Human epidermis samples were prepared according to standard protocols. The samples were obtained from abdominal skin of two 30-50 year old Eurasiatic donors. The samples were used as a membrane between the two chambers in the Franz cells. After about 6-8 hours, fat cells were carefully removed from the full thickness skin. The skin sections were cut into 2.5×2.5 cm squares, sealed in aluminum foil and frozen at −20° C. Prior to preparation, the samples were thawed to room temperature, immersed in 60° C. water, and the epidermis was gently separated from the remaining tissue with forceps and allowed to dry.

Skin Integrity

Before being mounted on the Franz cell, each epidermal sheet was visually inspected to avoid any possible defects. Additionally, the electrical resistance of isolated epidermis was measured to ensure the integrity of the barrier membrane. Epidermis samples with a resistance above 18 kΩ/cm$^3$ were used for experiments.

Skin Permeation

The upper and lower parts of the Franz cell were sealed with paraffin film and fastened together by a clamp. The membrane was positioned to act as a seal between the donor and receptor compartments. The skin was carefully mounted on the lower half of the Franz cell with the dermis facing downward and the stratum corneum in contact with the sample formulations. At the beginning of the experiment, the semisolid formulation was applied to the skin as donor phase (approximately 10 mg/0.636 cm$^2$) using an excavated silicon cylinder. The receiver compartments were filled with a saline solution, which had been filtered through a 0.2 μm membrane and sonicated under vacuum to remove air. Samples were prepared such that no air bubbles were present between the receptor medium and the dermis in the receptor compartment.

The prepared Franz cells were stirred continuously using a magnetic stir bar at a temperature of 37° C. At time points of 1, 3, 5, 7, and 24 hours, 0.2 mL samples were taken from the receiver compartment and replaced with fresh medium. Sink conditions were maintained throughout the experiments. Three replicates per test preparation per donor were performed. Samples from the receiver compartment were tested using gas chromatography to determine concentrations of compounds that permeated through the epidermis.

Epidermis Retention

Following the 24 hour permeation experiment described above, the epidermis samples were recovered and any residual formulation was removed from the surface of the epidermis, followed by a 10 mL methanol wash to remove any additional residual formulation. The epidermis samples were cut into small pieces and collected in tubes containing 5 mL of methanol. Samples were sonicated for 30 minutes and left to stand. After standing for 24 hours, the supernatant was centrifuged at 3000 rpm for 10 minutes at 23° C. and analyzed by HPLC.

Analysis of Dutasteride Concentration

Dutasteride concentration was determined using LC/MS-MS according to the following parameters:

Instrument: Acquity TQD (Waters) with ESI and triple quadrupole detector

Column: Poroshell 120 (Agilent) SB-C8 2.7 μm; 2.1×100 mm

Mobile Phase: Phase A (5 mM buffer, 0.1% formic acid/Phase B (acetonitrile)

Chromatographic Method: 20% Phase A/80% Phase B—isocratic for 7 minutes

Injection Volume: 10 μL

Column Temperature: 40° C.

Multiple Reaction Monitoring (MCM) was used for fragmentation at 529.4>95.27. Standards were prepared at concentrations of 10 5 and 1 μg/mL in methanol. Samples from the receiver compartment were injected without dilution.

Results—Dutasteride

In the receiver compartment, dutasteride was never detected, indicating that it did not permeate through human epidermis (skin) when subjected to the experimental conditions. The retained amounts of dutasteride in the human epidermis samples after 24 hours using the two different formulations were not statistically different. The results are summarized in Table 6 below.

TABLE 6

Permeation and retention data for dutasteride and human skin (n = 5)†

| | Permeated Amount After 24 hours (μg/cm$^2$) | Flux (μg/cm$^2$/h) | Retained Amount After 24 hours (μg/cm$^2$) | % retained |
|---|---|---|---|---|
| Siliconic Formulation | — | — | 1.65 ± 0.58 | 0.81 ± 0.28 |
| Spray Formulation | — | — | 1.00 ± 0.45 | 0.49 ± 0.22 |

†data reported as mean ± standard deviation

Example 6: Skin Permeation Assessment of Finasteride

Figure 4:
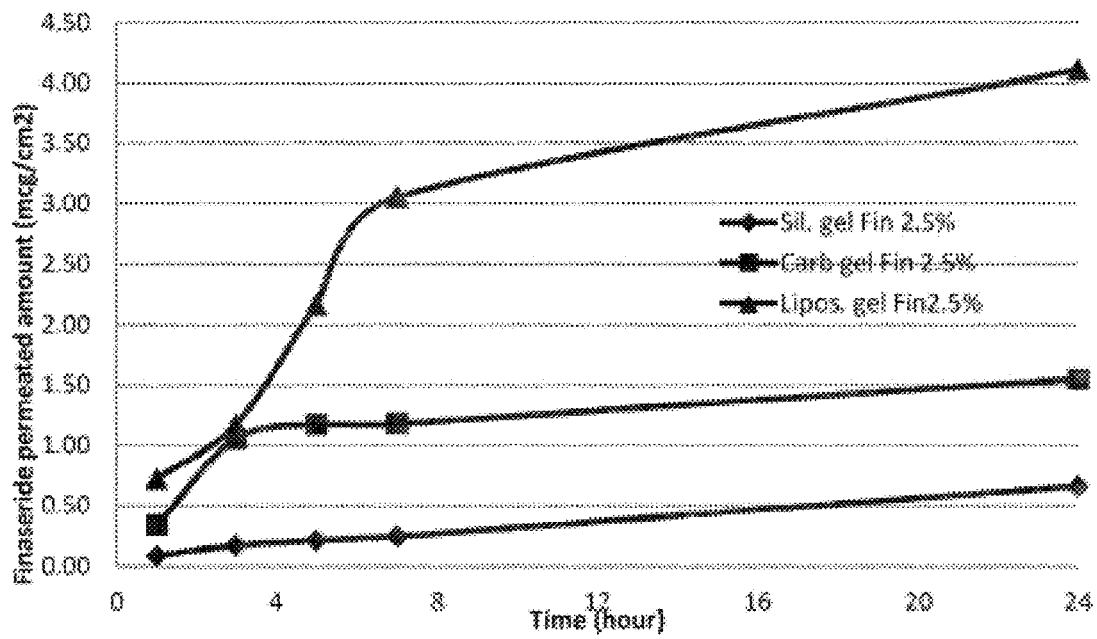
FIG. 4 depicts the finasteride permeation profiles through human epidermis using three types of formulations.

A skin permeation study was used to determine the permeation profile of finasteride through human skin (epidermis) in vitro. Samples were prepared and were tested according to the methods described in Example 5. Three different formulations were prepared, (1) a formulation prepared according to Example 1 ("Formulation 1"), (2) a carbomer-based gel without siliconic components or liposomes ("carb gel"), and (3) a liposome gel without siliconic components ("lipo gel"), each with a finasteride concentration of 2.5% w/w. Profiles for three different formulations through epidermis samples showed dramatically different permeation through epidermis as well as a calculated flux for Formulation 1 after 24 hours that was well below those of the other formulations tested (FIG. 4). It can be observed that Formulation 1 showed the lowest permeation profile and a calculated flux that was greatly reduced relative to the other formulations tested.

In order to compare the in vitro and in vivo data, an equation was used to calculate the steady-state plasma concentration of finasteride estimated on the basis of in vitro permeation data; the equation is given below:

$$C_{ss} = (A \times J)/CL$$

$C_{ss}$ is the steady state plasma concentration for finasteride, A is the skin area available for diffusion, J is the in vitro permeation rate (flux; μg/cm²h) and CL is the systemic clearance after oral administration (165 mL/minute for finasteride). The calculated $C_{ss}$ value for each formulation was compared to the maximum concentration at steady state ($C_{max}$) obtained after daily oral administration of 1 mg finasteride capsules.

The application area of the gel was assumed to be 200 cm² and the clearance value of 165 mL/minute was used to estimate the plasma steady state concentration ($C_{ss}$) from the in vitro experiments conducted with human skin from the same donor. These data are presented in Table 7 below.

TABLE 7

Permeation and retention data for finasteride and human skin†

| | Permeated Amount 24 h (μg/cm²) | Estimated In vivo Permeated Amount 24 h (μg/cm²) | Flux (μg/cm²/h) | $C_{ss}$ (ng/mL) | Retained Amount After 24 hours (μg/cm²) | Estimated In vivo Retained Amount 24 h (μg/cm²) |
|---|---|---|---|---|---|---|
| Formulation 1 | 0.66 ± 0.24 | 0.016 | 0.02 ± 0.00 | 0.49 | 0.41 ± 0.28 | 0.081 |
| Carb Gel | 1.55 ± 0.06 | 0.034 | 0.04 ± 0.01 | 0.74 | 0.34 ± 0.21 | 0.066 |
| Lipos Gel | 4.11 ± 1.50 | 0.241 | 0.13 ± 0.01 | 2.69 | 0.49 ± 0.39 | 0.095 |

†data reported as mean ± standard deviation

It was observed that when finasteride was administered to human skin in a formulation prepared according to embodiments of the present disclosure, the resulting steady state plasma concentration was between about 1.5- to 5.5-fold less than when administered according to other known topical formulations. It was also observed that the flux and amount of finasteride that permeated the skin was greatly reduced for formulations prepared according to embodiments of the present disclosure. As evidenced by the data in Table 7 and FIG. 4, these studies show the desirable "drug depot" qualities exhibited by the topical formulations prepared according to embodiments of the present invention.

Example 7: Topical Finasteride Study

A clinical study was performed to assess the efficacy associated with the finasteride formulation described in Example 3.

Patients in the study were positively identified as having androgenic alopecia (male pattern baldness). The degree of baldness was subsequently assessed according to the Norwood Hamilton Scale. Individuals with more advanced loss on this scale were selected, as changes is hair loss density and new hair growth would be more easily assessed in these cases. Exclusion criteria included the use of finasteride or any other hair loss treatment and/or hormonal therapy within the prior six months.

Patients were instructed to apply the 2.5% w/w finasteride topical liposomal topical gel to the areas of the scalp affected by pattern baldness massaging the gel into the scalp. The patients were instructed to apply the gel once daily after a morning shower, after having towel-dried the hair. Patients were instructed to not use hair-styling products during the course of the study.

All patients were informed of the known side-effects of oral finasteride. They were instructed to contact the physician conducting the study should they experience any of these side-effects. In addition, they were instructed to report any other symptoms experienced—including local issues at the site of gel application.

Follow-up assessments were initiated by patients once they had observed significant changes in their hair growth. Further follow-up assessments were performed at 6 monthly intervals, or time of visit of the study physician—depending on the patient's location. These assessments were documented using global photography of the scalp, focusing on areas affected by pattern baldness.

Results

Nine patients were selected for the purposes of this study. All nine patients demonstrated increased hair density and new follicular growth. Improvement was noted in both the frontal zone and vertex areas. The area with the most apparent increased density was along the inferior border of the posterior crown area (see FIG. 5A-5I). No side effects were reported during the study period, including a lack of sexual dysfunction or erectile dysfunction associated with oral finasteride.

Conclusion

The data demonstrate that the 2.5% w/w finasteride topical liposomal gel was highly effective in halting the progression of pattern baldness. Also, the data demonstrate marked regrowth of affected follicles. Surprisingly, no local or systemic adverse effects were identified as a result of the 2.5% w/w finasteride topical liposomal composition.

What is claimed is:

1. A liposomal topical formulation, comprising:
   a plurality of liposomes;
   an aqueous gel matrix in which the plurality of liposomes are dispersed, wherein the aqueous gel matrix comprises a gelling agent, a water-soluble silicone compound that is a PEG-X silicone or a PPG-X-silicone wherein X is an integer of 6-20, a polysilsesquioxane compound at a concentration of 1-20% by weight of the total composition, and water; and
   one or more active pharmaceutical ingredients (API) entrapped in the liposomes.

2. The liposomal topical formulation of claim 1, wherein the water-soluble silicone compound is a PEG-X silicone wherein X is an integer of 6-20.

3. The liposomal topical formulation of claim 2, wherein the water-soluble silicone compound is PEG-8 dimethicone.

4. The liposomal topical formulation of claim 1, wherein the polysilsesquioxane compound is a poly(alkylsilsesquioxane).

5. The liposomal topical formulation of claim 4, wherein the polysilsesquioxane compound is poly(methylsilsesquioxane).

6. The liposomal topical formulation of claim 1, wherein the polysilsesquioxane compound has a concentration ranging from 1 to 10% by weight of the total composition.

7. The liposomal topical formulation of claim 6, wherein the polysilsesquioxane compound has a concentration ranging from 5 to 10% by weight of the total composition.

8. The liposomal topical formulation of claim 6, wherein the polysilsesquioxane compound is present at 5% by weight of the total composition.

9. The liposomal topical formulation of claim 1, wherein the plurality of liposomes comprises lecithin.

10. The liposomal topical formulation of claim 1, wherein the one or more APIs comprises a 5-α-reductase inhibitor.

11. The liposomal topical formulation of claim 10, wherein the 5-α-reductase inhibitor is a 4-azasteroid compound.

12. The liposomal topical formulation of claim 11, wherein the 4-azasteroid compound is finasteride.

13. The liposomal topical formulation of claim 1, wherein the plurality of liposomes are at a concentration ranging from about 0.1 to 1.0% by weight of the total composition.

14. The liposomal topical formulation of claim 1, wherein the gelling agent has a concentration ranging from about 0.3 to 1.3% by weight of the total composition.

15. The liposomal topical formulation of claim 1, wherein the water-soluble silicone has a concentration ranging from about 6 to 14% by weight of the total composition.

16. A liposomal topical formulation base, comprising:
a plurality of liposomes; and
an aqueous gel matrix in which the plurality of liposomes are dispersed, wherein the aqueous gel matrix comprises a gelling agent, a water-soluble silicone compound that is a PEG-X silicone or a PPG-X-silicone wherein X is an integer of 6-20, a polysilsesquioxane compound at a concentration of 1-20% by weight of the total composition, and water.

17. A method of making the liposomal topical formulation of claim 1, comprising:
forming the plurality of liposomes, and
mixing the liposomes with the aqueous gel matrix and the one or more APIs,
wherein one or more of the APIs become entrapped in the liposomes.

18. A method of making the liposomal topical formulation base of claim 16, comprising:
forming the plurality of liposomes; and
mixing the liposomes with the aqueous gel matrix.

19. A method of making a liposomal topical formulation of claim 1, comprising:
combining the liposomal topical formulation base of claim 16 with one or more active pharmaceutical ingredients (API),
wherein one or more of the APIs become entrapped in the liposomes.

20. A method for treating or preventing a dermatological disorder, the method comprising administering to a patient in need thereof the liposomal topical formulation of claim 1.

21. The liposomal topical formulation of claim 6, wherein the polysilsesquioxane compound is poly(methylsilsesquioxane).

22. The liposomal topical formulation of claim 7, wherein the polysilsesquioxane compound is poly(methylsilsesquioxane).

23. The liposomal topical formulation of claim 22, wherein the one or more APIs comprise a 5-α-reductase inhibitor.

24. The liposomal topical formulation of claim 23, wherein the 5-α-reductase inhibitor is finasteride.

25. The liposomal topical formulation of claim 1, wherein the plurality of liposomes comprise a hydrogenated lecithin at a concentration of 0.5-1% (w/w), the gelling agent comprises a C10-C30 alkyl acrylate cross polymer, the water-soluble silicone compound is PEG-8dimethicone at a concentration in the range of 8-15% (w/w), the polysilsesquioxane compound is poly(methylsilsesquioxane) at a concentration ranging from 5 to 10% (w/w), and the one or more APIs comprise finasteride at a concentration of 2.5% (w/w) of the total weight of the formulation.

26. The liposomal topical formulation of claim 10, 12, 23 or 24, wherein the one or more APIs further comprise an anti-hypertensive vasodilator.

27. A method of treating androgenic pattern baldness, the method comprising administering to a human patient in need thereof the liposomal topical formulation of claim 10, 23 or 24.

28. The method of claim 27, wherein the liposomal topical formulation is administered twice a day, once a day or once every other day.

29. The method of claim 27, wherein the androgenic pattern baldness is male pattern baldness.

30. The method of claim 29, wherein the liposomal topical formulation is administered twice a day, once a day or once every other day.

* * * * *